(12) United States Patent
Wagner et al.

(10) Patent No.: US 7,807,864 B2
(45) Date of Patent: Oct. 5, 2010

(54) TRANSGENIC ANIMAL AS A MODEL FOR FIBROTIC DISEASES

(75) Inventors: Erwin Wagner, Vienna (AT); Robert Eferl, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 11/276,249

(22) Filed: Feb. 21, 2006

(65) Prior Publication Data

US 2006/0195916 A1 Aug. 31, 2006

(30) Foreign Application Priority Data

Feb. 22, 2005 (EP) ................ 05 003 759

(51) Int. Cl.
*A01K 67/027* (2006.01)
*C12Q 1/00* (2006.01)
*G01N 33/48* (2006.01)

(52) U.S. Cl. .......... 800/18; 435/4; 435/7; 435/21; 436/63

(58) Field of Classification Search ........ 435/4, 435/7.21; 436/63; 800/18
See application file for complete search history.

(56) References Cited

U.S. PATENT DOCUMENTS 6,492,129 B1 * 12/2002 Grotendorst .......... 435/7.21

OTHER PUBLICATIONS

Pope, J.E., Curr. Op. Rheumatol. 14: 704-710, 2002.*
Chua et al, Am. J. Respir. Cell. Mol. Biol. 33: 9-13;2005.*
Racay, Bratisl Lek Listy, 103: 121-126, 2002.*
Sigmund, Arteroscler. Throm. Vasc. Biol. 20: 1425-1429, 2000.*
Sandgren et al, Mol. Cell. Biol. 13(1): 320-330, 1993.*
Jhappan et al, Cell 61: 1137-1146, 1990.*
Kuroiwa et al, Nature Genetics 36(7):775-80, 2004.*
Moreadith et al, J. Mol. Med. 75(3): 208-216, 1997.*
Kappell et al, Current Opinion in Biotechnology 3: 549-553, 1992.*
Mullins et al, Hypertension 22: 630-633, 1993.*
Houdebine, J. Biotech. 34: 269-287, 1994.*
Cameron, Molec. Biotech. 7: 253-265, 1997.*
Polejaeva et al, Theriogenology, 53(1):117-126, 2000.*
Rulicke et al, Experimental Physiology 85: 589-601, 2000.*
Mullins et al, Journal of Clinical Investigation 97(7): 1557-1560, 1996.*
Pearson, Nature 415(6867):8-9, 2002.*
Bishop, Reprod. Nutr. Dev. 36: 607-618, 1998.*
Denning, Nat. Biotech. 19:559-562, 2001.*
Humpherys et al, Science 293:95-97, 2001.*
Wall et al, J Dairy Sci. 80:2213-2224, 1997.*
Yanagimachi, Mol. Cell Endocrinol. 187:241-248, 2002.*
Wall, Theriogenology 45: 57-68, 1996.*
Molven et al, Genomics 38(1):7-75, 1996.*
Tokugawa et al, Mol. Immunol. 34(18):1263-1272, 1997.*
Kaushansky et al, PNAS 86(4):1213-1217, 1989.*
Chen et al, Cell Tissue Res. 329(1):169-178, 2007.*
Ruther et al, Cell 53:847-856, 1988.*
Jochum et al, Nature Medicine 6(8):980-984, 2000.*
Nishina et al, PNAS 87:3619-3623, 1990.*
Foletta et al, Oncogene 9:3305-3311, 1994.*
Means et al, Gastroenterology 124:1020-1036, 2003.*
Denton et al, J. Biol. Chem. 278(27):25109-25119, 2003.*
Kolb et al, Am. J. Respir. Cell Mol. Biol. 27(2):141-150, 2002.*
McHenry, Jane, Z.; Overexpression of fra-2 in transfenic mice perturbs normal eye development; Oncogene, vol. 17, No. 9, Sep. 3, 1998, pp. 1131-1140, XP002323126.
Schorpp, M., The human ubiquitin C promoter directs high ubiquitous expression of transgenes in mice; Nucleic Acids Research, Oxford University Press, Surrey, GB; vol. 24, No. 9, May 1, 1996; pp. 1787-1788; XP002121787.
Timblin, Cynthia; Ultrafine airborne particles cause increases in protooncogene expression and proliferation in alveolar epithelial cells; Toxicology and Applied Pharmacology, vol. 179, No. 2, Mar. 1, 2002; pp. 98-104, XP002313127.
Grigoriadis, A.E.; Osteoblasts are target cells for transformation in c-fox transgenic mice; Journal of Cell Biology, Rockfeller University Press, NY, NY, U.S., vol. 122, No. 3, Aug. 1993, pp. 685-701, XP002953461.

* cited by examiner

*Primary Examiner*—Kevin K. Hill
(74) *Attorney, Agent, or Firm*—Michael P. Morris; Mary-Ellen M. Devlin; Anthony P. Bottino

(57) ABSTRACT

Disclosed is a transgenic non-human animal with broad or cell type-specific ectopic expression of fra-2 that manifests itself in a fibrotic disease, methods for obtaining such animal and their use. Fra-2 transgenic animals, in particular mice, are useful as model systems for human fibrotic disease, e.g. lung scleroderma and pulmonary fibrosis. Cells obtained from the animal are useful for the analysis of fibrotic disease and for testing compounds useful in the therapy of fibrotic disease.

9 Claims, 14 Drawing Sheets

Figure 6B,C,D
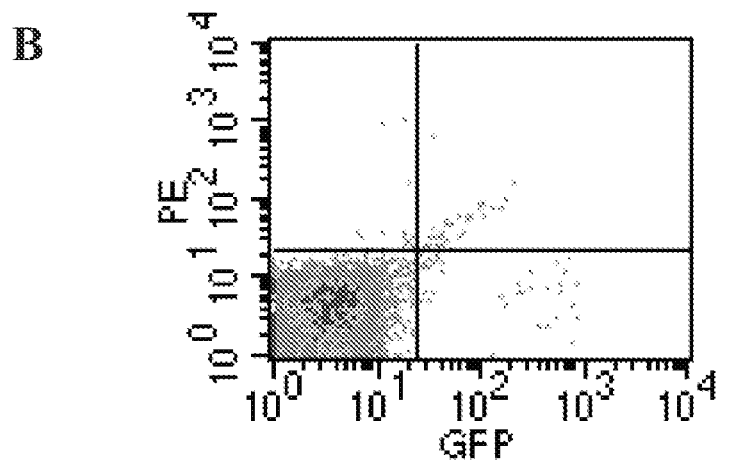
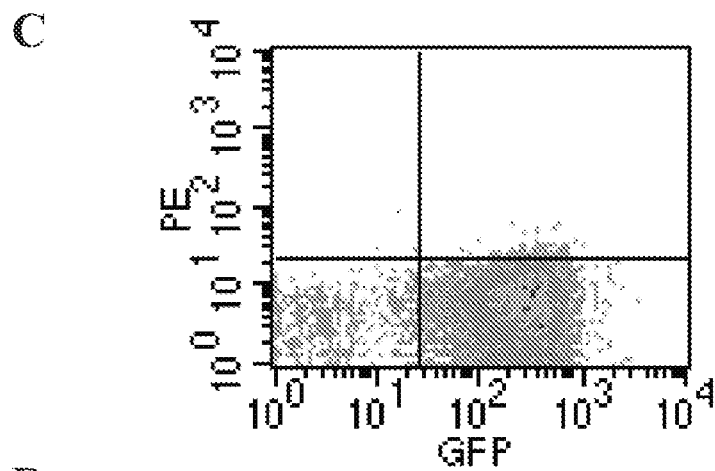
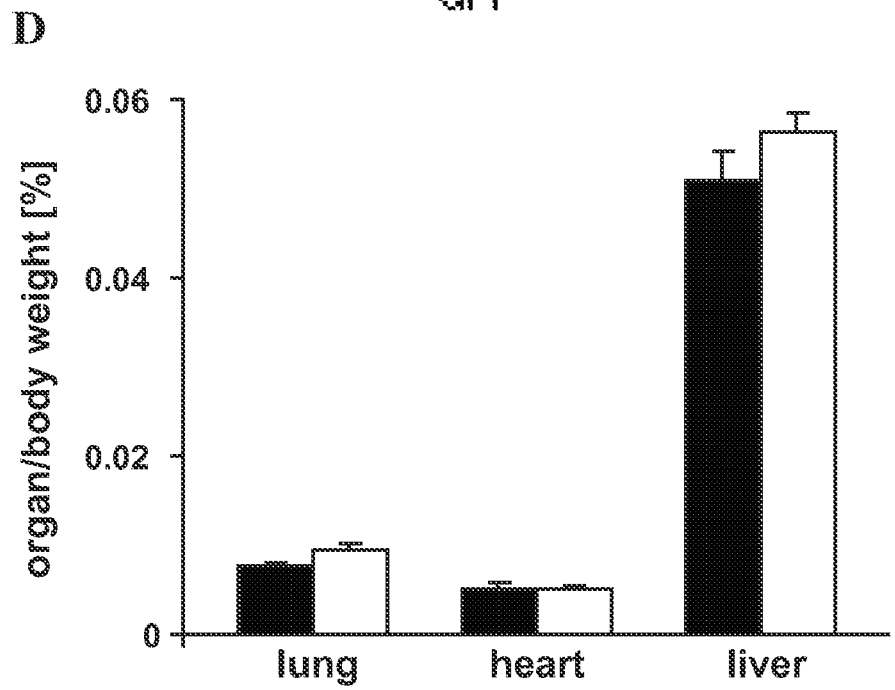

Figure 7B,C,D
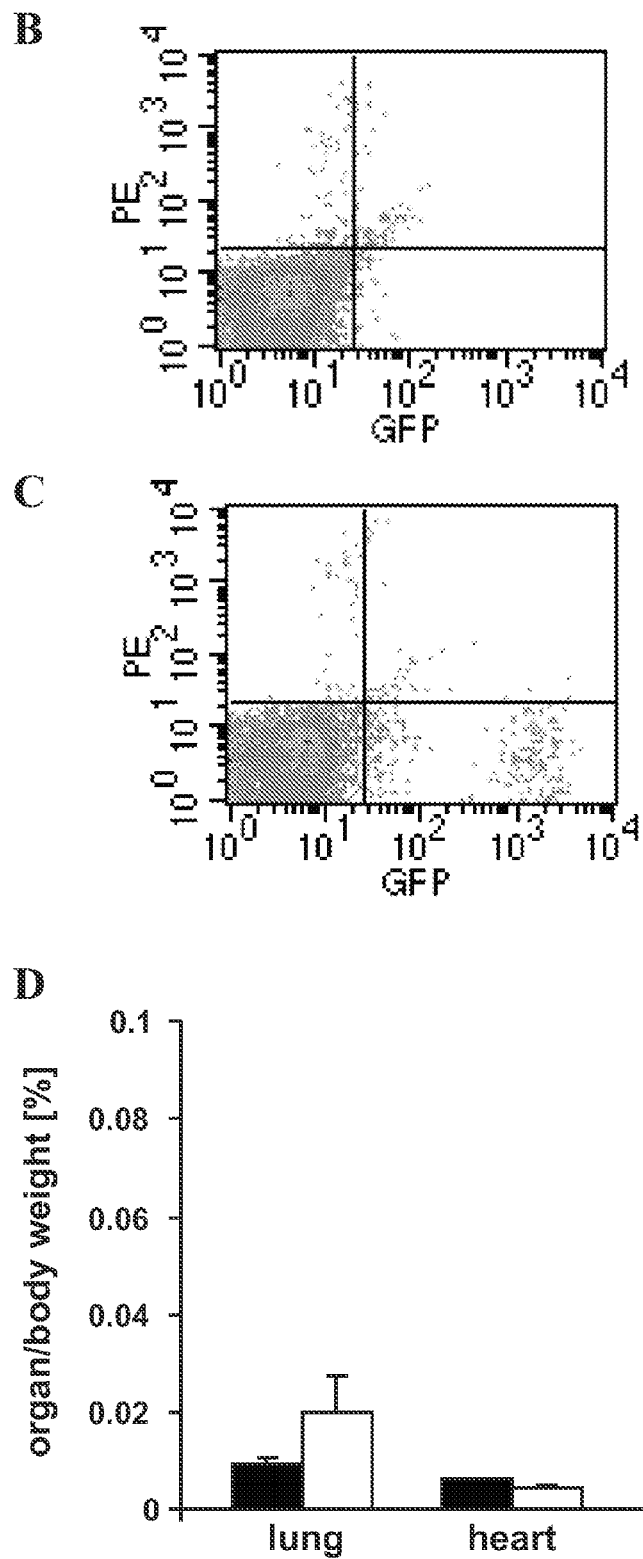

Fig. 8A,B
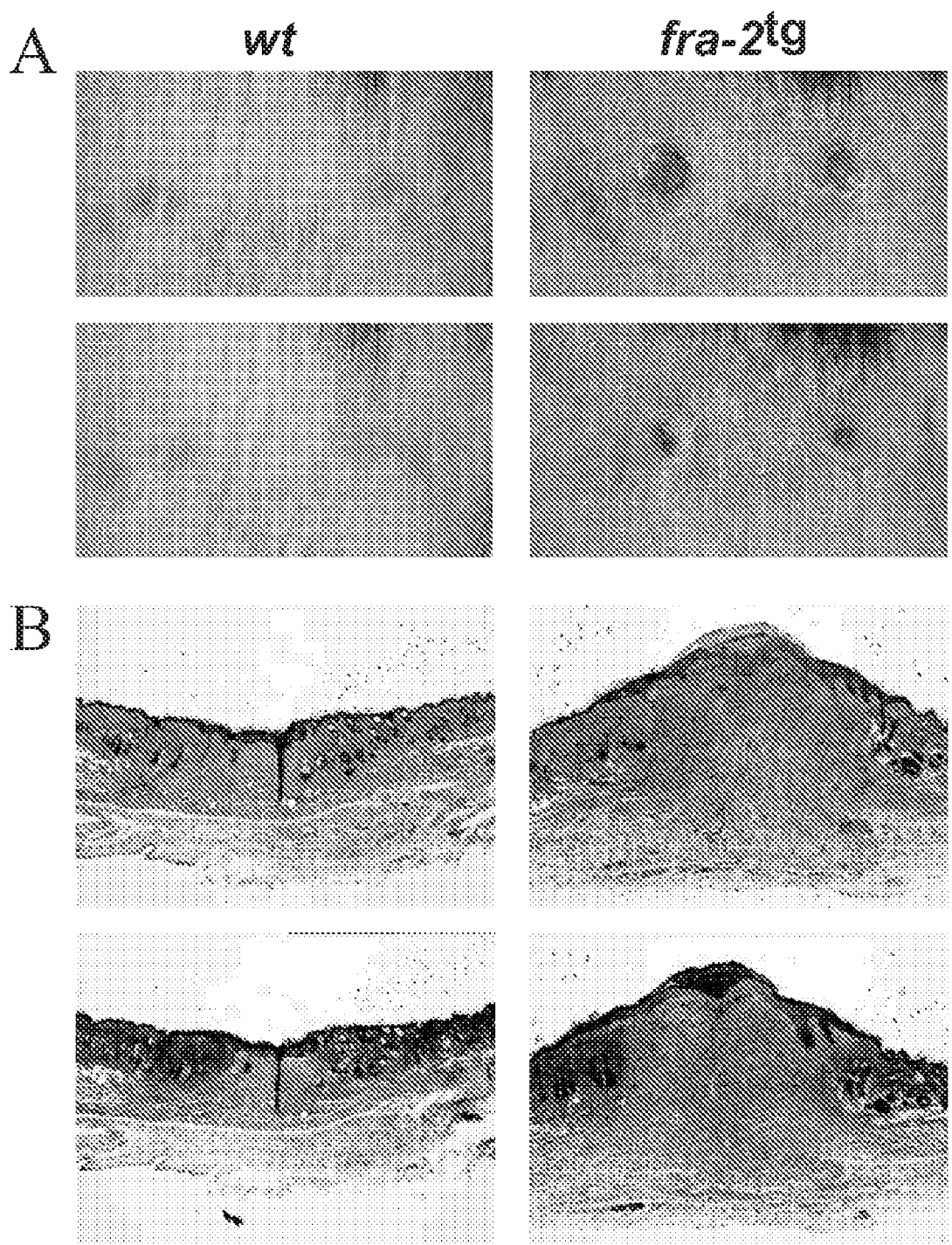

Fig. 8 D,E,F,G
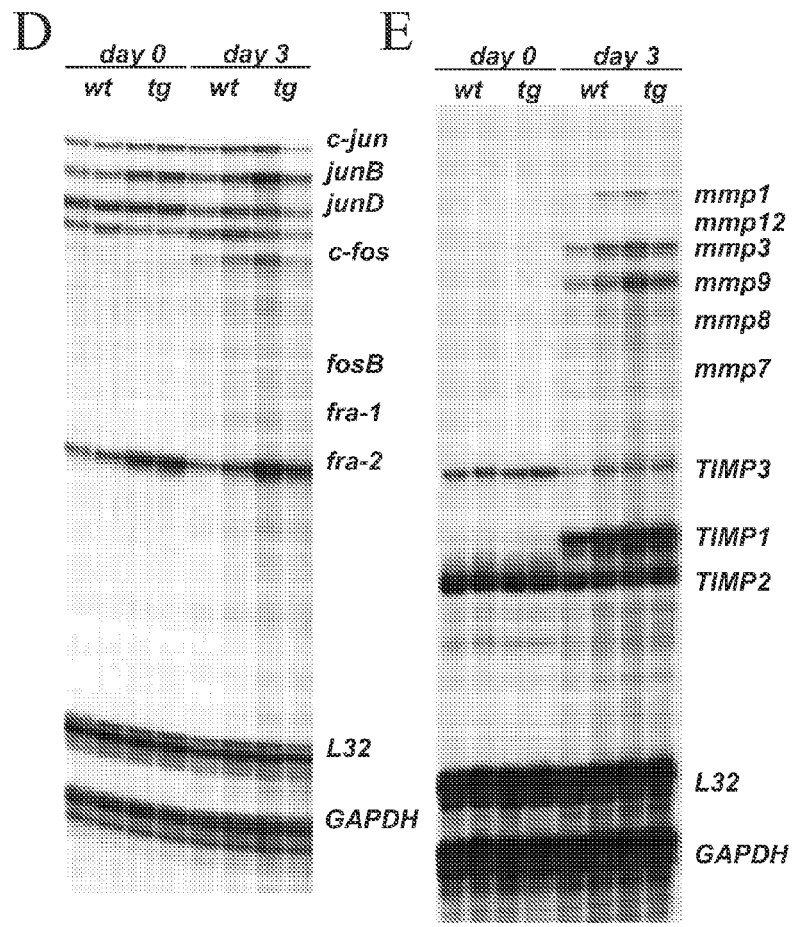
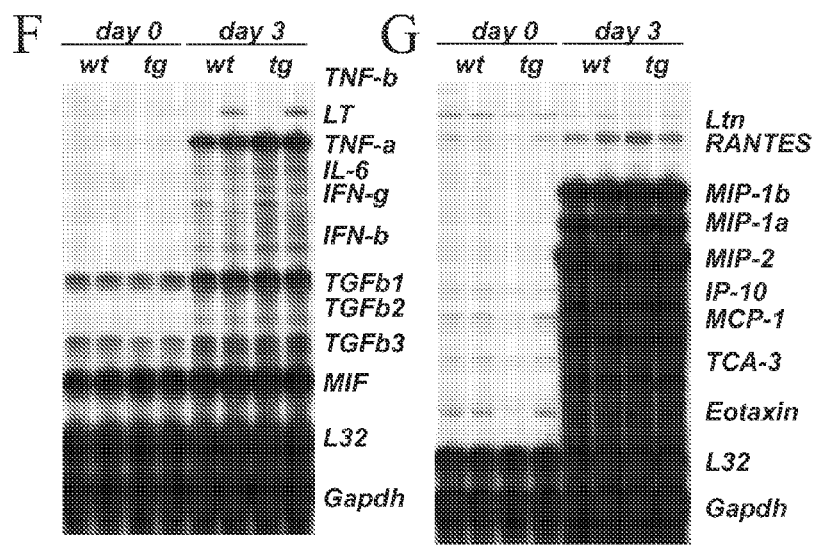

TRANSGENIC ANIMAL AS A MODEL FOR FIBROTIC DISEASES

APPLICATION DATA

This application claims benefit to EP 05 003 759.7 filed Feb. 22, 2005.

FIELD OF INVENTION

The invention relates to animal models, in particular mouse models, for fibrotic diseases like pulmonary fibrosis and fibrotic disorders of the skin.

BACKGROUND

Pulmonary fibrosis is a devastating disorder that affects five million people worldwide. However, the actual numbers may be significantly higher as a possible consequence of misdiagnosis. Typically, patients develop pulmonary fibrosis in their forties and fifties with symptoms that include shortness of breath, chronic cough, fatigue, loss of appetite and rapid weight loss. The mean survival time following diagnosis is less than 5 years (Giri, 2003). Pulmonary fibrosis is not seen as a separate entity but develops usually in the context of environmental exposures or as an accompaniment of a syndrome. Common causes are exposure to asbestos, metal dusts or organic substances, sarcoidosis (a disease characterized by the formation of granulomas), exposure to medical drugs and radiation. Often pulmonary fibrosis is associated with connective tissue or collagen diseases such as rheumatoid arthritis and scleroderma (Giri, 2003).

Pathologically, the disease is characterized by chronic inflammation and collagen production within fibroblastic foci in the lung.

Myofibroblasts, a distinguishing feature of fibroblastic foci, are thought to arise from local activation of parenchymal fibroblasts by transforming growth factor β (TGF-β) stimulation and are historically considered to be the collagen-producing cell in fibrotic lesions (Selman and Pardo, 2003); in addition, CTGF (connective tissue growth factor) is considered a very important factor and is required for differentiation and collagen gene expression. However, recent findings have questioned this fundamental concept and suggested a hematopoietic origin of the pathological fibroblasts (Hashimoto et al., 2004). The disease typically proceeds with scarring of the lung and the alveoli which become lined by fibrotic tissue. When the scar forms, the tissue becomes thicker causing an irreversible loss in efficiency of the tissue's ability to transfer oxygen into the bloodstream (Gross and Hunninghake, 2001).

Several growth factors have been implicated in the pathogenesis of pulmonary fibrosis. These factors have been identified by virtue of their ability to stimulate fibroblast division and extracellular matrix (ECM) production, as well as their presence in the lungs and lung fluids of patients or animals with fibrotic lung disease. These growth factors include TGF-β, insulin-like growth factor (IGF)-I, platelet-derived growth factor (PDGF), members of the fibroblast growth factor (FGF) family and keratinocyte growth factor (KGF) (Krein and Winston, 2002).

There are currently no effective treatments or a cure for pulmonary fibrosis. The pharmacological agents designed to treat lung scarring are still in the experimental phase. Although traditional theories have postulated that it might be an autoimmune disorder, the treatments intended to suppress inflammation have only limited success in reducing the fibrotic progress (Giri, 2003). Since pulmonary fibrosis is a very complex disease, the prediction of longevity of patients after diagnosis varies greatly.

It is still a matter of debate if pulmonary fibrosis is primarily caused by chronic inflammation (Gross and Hunninghake, 2001). Originally, experimental evidence suggested that fibrotic lung diseases are inflammatory disorders at their inception. For example, pulmonary fibrosis develops in mice with ectopic expression of the inflammatory mediator tumor necrosis factor α (TNF-α) in the lung (Miyazaki et al., 1995). Additionally, in a bleomycin model of pulmonary fibrosis in the mouse, the fibrosis is preceded by profound inflammation, including the production of high levels of TNF-α (Piguet et al., 1989). Importantly, TNF-α-deficient or TNF-α receptor-deficient mice are resistant against bleomycin-induced pulmonary fibrosis (Ortiz et al., 1998; Piguet et al., 1997). These results led to the assumption that fibrosis might be avoided when the inflammatory cascade is interrupted before irreversible tissue injury occurred. Thus, this theory explains the initial enthusiasm for corticosteroid and cytotoxic therapy of pulmonary fibrosis. However, it is now clear that the current anti-inflammatory therapy provides little benefit (Giri, 2003). Therefore, some studies have attempted to show that fibrotic lung disorder is not an inflammatory disorder. For example, development of fibrotic lung disease can be triggered by adenoviral transfer of TGF-β to the lungs of animals with only a transient inflammatory response. These new insights suggest that pulmonary fibrosis results from sequential lung injury with a subsequent wound healing response rather than chronic injury. Therefore, a therapeutic strategy based on modification of fibroblast replication and matrix deposition is established. However, no beneficial clinical effect was seen in patients after colchicine treatment (interferes with intracellular collagen processing) or penicillamine treatment (collagen cross-link inhibitor). Other agents that are in experimental trials to block fibrogenesis include pirfenidone, interferon γ or antibodies against TGF-β signaling (Giri, 2003).

Consequently, there is a need for an efficient and reliable animal model for the study of fibrotic diseases, e.g. pulmonary fibrosis, and for testing drug candidates for the treatment of such disorders.

SUMMARY

It has therefore been an object of the invention to provide an animal model for fibrotic disease, e.g. pulmonary fibrosis that develops in the context of scleroderma-like disease (generalized fibrosis), or other fibrotic diseases.

Figure 1:
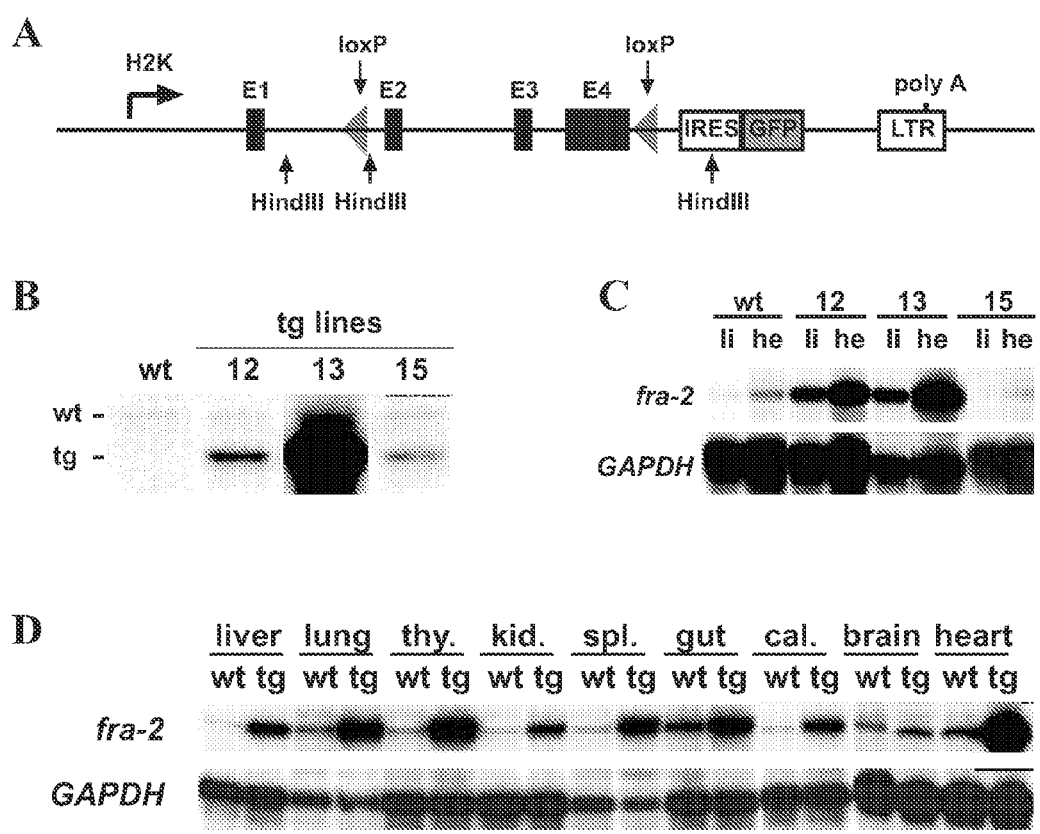
FIG. 1
A.) Schematic scheme of the fra-2 transgenic vector. An H2k$^b$ promoter is used for fra-2 expression. The IRES-EGFP reporter gene behind fra-2 is used to monitor transgene activity and a LTR sequence is included for mRNA stabilization. The loxP sites allow Cre-recombinase-mediated deletion of the transgene. H2K$^b$: H2Kb promoter; E1-E4: Exon 1-4 of fra-2; polyA: polyadenylation signal; Hind III: restriction sites used for Southern blot analysis.
B.) Southern blot analysis of three transgenic lines (12, 13, 15) to determine the copy number of transgene in the genome. DNA from mouse tails is digested with Hind III and probed with a sequence corresponding to exon 2 of fra-2. The positions of the wild-type and transgenic bands are indicated. Quantitation revealed 4, 60 and 2 transgenic copies for transgenic lines 12, 13 and 15, respectively.

C.) RNase protection assay for fra-2 expression with two tissues (liver and heart) from transgenic lines 12, 13 and 15. Expression of fra-2 is elevated in lines 12 and 13 in both tissues to a similar extend. No transgene expression is detectable in transgenic line 15. Expression of GAPDH is used as a loading control.

D.) RNase protection assay with different tissues of adult (6 week-old) transgenic mice (line 13). The transgene is expressed ubiquitously except for the brain. thy.: thymus; kid.: kidney; spl.: spleen; cal.: calvariae.

FIG. 2

A.) A Kaplan Meier plot showing premature lethality of fra-$2^{tg}$ mice. Mice with high expression of the fra-2 transgene (lines 12 and 13) become sick at adulthood and start to die around 6 weeks of age. No premature lethality is seen in mice of line 15 which showed no expression of the transgene.

B.) Increased lung to body weight ratios in fra-$2^{tg}$ mice. An increase of lung weight is observed in transgenic mice of line 12 and 13 (here shown for line 12) but not line 15. The major increase of lung weight coincides with lethality of transgenic mice. Sickness is judged by loss of body weight, appearance of the fur, weakness of mice and shortness of breath.

FIG. 3

A.) Gross morphology of fra-$2^{tg}$ lungs. Mice of line 12 and 13 show dramatically increased lungs with apparent fibrosis.

B.) H&E-stained sections of fra-$2^{tg}$ lungs. Mice of line 12 and 13 show interstitial lung fibrosis (upper panel) and stenosis of blood vessels (lower panel).

FIG. 4

A.) A scleroderma-like syndrome develops in fra-$2^{tg}$. Chromanilineblue-staining for collagen (in blue) revealed that fibrotic lesions in fra-$2^{tg}$ mice are not restricted to the lung but can also be observed in other organs (liver, skin and heart are shown as examples).

B.) Realtime PCR analysis of collagen expression in the lungs of fra-$2^{tg}$ mice. Expression of fibrogenic collagen type I and type III is increased in the lungs of sick mice.

FIG. 5

A.) Pulmonary fibrosis in fra-$2^{tg}$ mice starts with vascular and perivascular immigration of inflammatory cells. H&E-staining of fra-$2^{tg}$ lungs demonstrates inflammation as the first event in pulmonary fibrosis (upper panel). Inflammatory cells are mainly composed of CD3-positive T-cells (black staining, arrowheads) and esterase-positive myeloid cells such as granulocytes (red staining, arrowheads).

B.) Inflammation causes accumulation of chemokines and cytokines in the lungs of fra-$2^{tg}$ mice as demonstrated by RNase protection assay.

FIG. 6

A.) No severe pulmonary fibrosis in wild-type mice reconstituted with fra-$2^{tg}$ bone marrow. Lung and liver sections of wild-type mice reconstituted with fra-$2^{tg}$ bone marrow after lethal irradiation demonstrate that the fibrosis cannot be easily transplanted.

B.) FACS profile of bone marrow cells from wild-type mice reconstituted with wild-type bone marrow.

C.) FACS profile of bone marrow cell from wild-type mice reconstituted with fra-$2^{tg}$ bone marrow. Note that almost all bone marrow cells express the EGFP reporter gene reflecting transgene expression.

D.) Organ/body weight ratios confirm that no severe pulmonary fibrosis develops in wild-type mice reconstituted with fra-$2^{tg}$ bone marrow.

FIG. 7

A.) Severe pulmonary fibrosis in fra-$2^{tg}$ mice reconstituted with wild-type bone marrow. Lung and liver sections of fra-$2^{tg}$ mice reconstituted with wild-type bone marrow after lethal irradiation demonstrate that the fibrosis develops in the presence of wild-type bone marrow.

B.) FACS profile of bone marrow cells from wild-type mice reconstituted with wild-type bone marrow.

C.) FACS profile of bone marrow cell from fra-$2^{tg}$ mice reconstituted with wild-type bone marrow. Note that almost all transgenic EGFP-positive cells have disappeared.

D.) Organ/body weight ratios confirm that pulmonary fibrosis developed in fra-$2^{tg}$ mice reconstituted with wild-type bone marrow.

FIG. 8

A.) Delayed wound healing after full-thickness wounding of fra-$2^{tg}$ mice. Fra-2 transgenic mice show delayed wound closure after full-thickness wounding of the backskin (upper panel: 8 days after wounding, lower panel: 11 days after wounding).

B.) An increased amount of granulation tissue consisting of collagen is visible in the wounds of fra-2 transgenic mice (11 days after wounding; upper panel: H&E-staining; lower panel: CAB-staining for collagen in blue).

C.) Quantification of wound healing demonstrates delayed wound closure in fra-2 transgenic mice starting as early as 3 days after wounding.

D.-G.) Rnase protection assays with skin biopsies taken at wounding and 3 days after wounding. No difference in expression of AP-1 members except for fra-2 (D), matrix metalloproteinases (E), TIMPs (E), cytokines (F), TGF-beta family members (F) and chemokines (G) can be observed.

DETAILED DESCRIPTION

The solution of the problem underlying the invention is based on the molecular mechanisms associated with the transcription factor AP-1.

The transcription factor AP-1 is generated by a series of dimers of products of the Fos, Jun, and CREB/ATF protein families (Eferl and Wagner, 2003), as well as other bZip proteins. In addition, associations have been observed between Fos or Jun and the p65 subunit of NFκB (Stein et al., 1993), and ATF-2 and p50-NFκB (Du et al., 1993). Combinatorial association can draw on three Jun genes (c-jun, junB, junD), four Fos genes (c-fos, fosB, fra-1, fra-2) and several CREB/ATF genes (Eferl and Wagner, 2003). Despite the high degree of homology in the overall structural features, the different members of the Fos, Jun and CREB families exhibit significant differences, which lead to subtle differences in DNA binding and transcriptional activation suggesting specific functions in gene regulation for individual dimers (Jochum et al., 2001). The members of the AP-1 family are engaged in the control of cell proliferation as well as various types of differentiation, and also in neural function and stress responses. AP-1 is one of the key factors that translate external stimuli both into short- and long-term changes of gene expression (Jochum et al., 2001).

Both, Jun and Fos protein family members are required for bone formation and remodelling. Ubiquitous partial deletion of a conditional c-jun allele leads to malformations of the axial skeleton (Behrens et al., 2003) and JunB has recently been shown to be essential for osteoblast (the bone-forming cell) proliferation and differentiation (Kenner et al., 2004). Most Fos proteins are implicated in proliferation and differentiation of osteoblasts and osteoclasts (bone-resorbing cell). Transgenic mice expressing c-Fos develop osteosarcomas due to increased osteoblast proliferation (Grigoriadis et al., 1993). In contrast, mice lacking c-Fos develop osteopetrosis caused by a differentiation defect in the osteoclast lineage (Grigoriadis et al., 1994; Wang et al., 1992). This differentiation defect can be rescued by expression of the Fos-related protein Fra-1 suggesting that Fos and Fra-1 have overlapping functions in osteoclast differentiation (Fleischmann et al., 2000). Loss of Fra-1 in a conditional mouse model leads to reduced bone mass due to a functional defect of osteoblasts (Eferl et al., 2004). Consistently, ectopic Fra-1 expression leads to osteosclerosis likely due to accelerated differentiation of osteoprogenitors into mature osteoblasts (Jochum et al., 2000). A similar skeletal phenotype was described in transgenic mice expressing ΔFosB, a splice-variant of FosB, suggesting that Fra-1 and ΔFosB promote osteoblast differentiation by regulating common transcriptional target genes in the osteoblast lineage (Sabatakos et al., 2000). However, the requirement of Fra-2 in bone formation is less clear. Conditional deletion of Fra-2 in chondrocytes leads to reduced bone mass (Karreth et al., 2004) but no loss or gain of function studies have been performed in osteoblasts or osteoclasts.

"Ectopic expression" designates the occurrence of gene expression in a tissue in which such gene is normally not expressed or normally expressed at a lower level.

In the experiments leading to the invention, the genomic locus of Fra-2 was broadly overexpressed in a transgenic mouse (fra-$2^{tg}$), originally with the purpose to investigate the consequence of increased Fra-2 activity on osteoblast and osteoclast functions. The transgenic vector for the fra-$2^{tg}$ mice was designed in a similar way as for c-fos$^{tg}$ and fra-$1^{tg}$ mice (Grigoriadis et al., 1993; Jochum et al., 2000) to allow a meaningful comparison of the three transgenic mouse models.

While experiments with previously described fra-2 transgenic mouse (Mc Henry et al., 1998) showed that overexpression of fra-2 in perturbs normal eye development, it was surprisingly found in the experiments of the invention that overexpression of fra-2 results in a phenotype resembling human pulmonary fibrosis. Surprisingly, the fra-2 transgenic mice die within 6 months because they develop a generalized fibrosis which mainly affects the lung. In addition to pulmonary fibrosis, it has been shown in the experiments of the invention that fra-$2^{tg}$ mice develop fibrosis in several other tissues leading to a scleroderma-like phenotype.

Thus, the invention relates to a an animal model for fibrotic diseases, comprising a non-human transgenic mammal, in particular a rodent, with broad or cell type-specific ectopic expression of fra-2 that manifests itself in a phenotype of a fibrotic disease.

The term "fibrotic diseases" relates to diseases involving fibrosis, which may e.g. be due to chronic inflammation or repair and reorganization of tissues. Fibrosis is the formation or development of excess fibrous connective tissue in an organ or tissue as a reparative or reactive process, as opposed to formation of fibrous tissue as a normal constituent of an organ or tissue, including the kidneys, heart, lungs, liver, skin and joints.

In a preferred embodiment, the fibrotic disease is a pulmonary disease, in particular pulmonary fibrosis.

In the meaning of the present invention, the term "pulmonary disease" encompasses lung (pulmonary) fibrosis and pulmonary diseases with a fibrotic component selected from idiopathic pulmonary fibrosis, other interstitial pneumonias (IP) such as giant cell interstitial pneumonia, non-specific IP, cryptogenic organizing pneumonia, collagen vascular disease-associated IP, and drug-induced IP, also sarcodosis, cystic fibrosis, respiratory distress syndrome, granulomatosis, silicosis, asbestosis, systemic scleroderma involving the lung, as well as fibrosis and remodeling in asthma or COPD.

In a further embodiment, the fibrotic disease is generalized fibrosis, which is a skleroderma-like fibrosis that manifests itself in several target organs, including, without limitation, besides lung and/or skin, the spleen, heart, kidney and/or liver.

It has also been shown in the experiments of the invention that fra-$2^{tg}$ mice develop fibrotic disorders of the skin, which are associated with excessive healing. Keloids and hypertrophic scars in the skin are examples of such fibrotic skin disorders.

Full thickness wound healing experiments of the mouse back skin demonstrated that wound closure is delayed in fra-$2^{tg}$ mice, which is due to excessive production of granulation tissue in the closing wounds and leads to excessive scar formation.

Thus, in a further aspect, animal model of the invention is also useful as a model for fibrotic skin disorders.

By "transgenic rodent" is meant a rodent (e.g., mouse, rat, hamster, etc.) having a non-endogenous (i.e., heterologous) nucleic acid sequence encoding Fra-2 DNA stably integrated into its germ line (i.e., in the genomic sequence of most or all of its cells). Alternatively, a fra-2 transgene can be introduced into embryonic stem cells for generation of chimaeric mice with ectopic expression of fra-2.

In a preferred embodiment, the rodent is a mouse.

Heterologous Fra-2 nucleic acid is introduced into the germ line of such animals by genetic manipulation of, for example, embryos or embryonic stem cells of the host animal according to standard protocols.

In the following, the fra-2 transgenic rodent/mouse is referred to as "fra-$2^{tg}$" rodent/mouse.

For clarity, the term "fra-$2^{tg}$ mouse", or "fra-$2^{tg}$ rodent", respectively, in the meaning of the present invention, is a transgenic rodent/mouse carrying a fra-2 genomic locus or fra-2 cDNA, under the control of a promoter that allows broad or cell-type specific transgene expression.

By "fra-2" (or "Fra-2" respectively) is meant fra-2 DNA (or Fra-2 protein, respectively) from any mammalian species that results, when expressed under the control of a suitable promoter at the proper level and location such that it manifests itself in the phenotype of interest, i.e. fibrotic disease, in particular pulmonary fibrosis. The chosen fra-2 DNA may be identical to the endogenous fra-2 gene of the selected animal species (e.g. a mouse carries the murine fra-2 DNA transgene and a rat the rat fra-2 transgene) or it may be different, e.g., in particular in view of the use of the animal as a model for human disease and for screening or characterizing inhibitors for human disease, it may be human fra-2.

The fra-2/Fra-2 DNA/protein sequences are known from the literature, e.g. from human (GenBank Accession No. X16706; Matsui et al., 1990), mouse (GenBank Accession No. NM_008037; Foletta et al., 1994) or rat (GenBank Accession No. NM_012954).

In the experiments of the invention, the constituents H2-K$^b$ (promoter), IRES-EGFP (reporter gene) and LTR (enhancer) were used for the transgenic construct; these elements can be replaced by other elements, provided that expression of the transgene at the level and location in the body is such that it manifests itself in the phenotype of interest. Examples for ubiquitous promoters suitable for transgene expression are the ubiquitin C promoter, the CMV promoter/enhancer, the Pgk-1 promoter or the chicken β-actin promoter (Schorpp et al., 1996). Examples for reporter systems suitable for monitoring transgene expression are β-galactosidase, EGFP, EYFP, ERFP. An example for a suitable enhancer element that may be optionally present in the construct to ensure broad expression of fra-2 is the long terminal repeat (LTR) from FBJ murine osteosarcoma virus.

In the experiments leading to the invention, the following experimental system was used: First, a genomic mouse λ DNA library (from mouse strain 129 Sv) was screened for the mouse fra-2 gene with labeled oligonucleotides binding to the four exons of fra-2. The fra-2 full-length locus was isolated, characterized and sequenced. The sequence of the four exons matched completely with the published mouse Fra-2 cDNA sequence (Foletta et al., 1994). The promoter for the major histocompatibility complex class I antigen H2-$K^b$ (Grigoriadis et al., 1993) was cloned in front of the fra-2 genomic locus to allow ubiquitous transgene expression. To monitor transgene activity in vivo, an IRES-EGFP (Zhu et al., 1999) sequence was cloned behind the fra-2 locus followed by the long terminal repeat (LTR) sequence of the FBJ-murine sarcoma virus to stabilize fra-2 mRNA and to ensure transgene expression in mesenchymal cells (Grigoriadis et al., 1993). In addition, loxP sites were placed in front of exon 2 and after exon 4 to allow Cre-mediated deletion of transgene multimers and generation of several transgenic lines with different transgene copy numbers and levels of transgene expression.

The fra-$2^{tg\ rodents}$, in particular mice, can be obtained with methods based on known protocols for generating transgenic animals, e.g. by using the Cre-loxP mediated gene manipulation (as described e.g. by Orban et al., 1992; Sauer, 1993), by microinjection of fra-2 transgenes into fertilized oocytes, injection of large transgenes based on bacterial artificial chromosomes (BACs) into fertilized oocytes (as e.g. described by Chrast et al., 1999; Hong et al., 2001), infection of 8 cell stage embryos with retroviral (Blesch, 2004) or other vectors carrying the transgene, such as adenoviral (Lai et al., 2002) and lentiviral-mediated (Blesch, 2004) somatic transgenesis, transfection or infection of embryonic stem (ES) cells with constructs carrying the transgene (Wolf and Woodside, 2005).

In a further aspect, the present invention relates to a rodent, e.g. a mouse, with ectopic expression of fra-2 in lung cells, e.g. airway epithelial cells, fibroblasts, myofibroblasts and hematopoietic cells, as an animal model for pulmonary fibrosis. To obtain ectopic expression in these specific cell types, cell-type specific promoters are used for generating the transgenic animal, e.g. surfactant protein C (Boggaram, 2003) promoter for airway epithelial cells, or the CD4 promoter (Tanigaki et al., 2004), the CD19 promoter (Rickert et al., 1997), the LysM promoter (Clausen et al., 1999) for hematopoietic cells or the pro-alpha 1(I) collagen promoter for fibroblasts (Rossert et al., 1995). In addition to these cell types, ectopic expression may be desirable in other cells that are relevant for the phenotype of interest. In analogy to the above-mentioned cells, fra-2 expression can be achieved by directing expression of the transgene in these cells by using a cell-type specific promoter.

In a further aspect, the invention relates to transgenic rodent cells, in particular mouse cells, which have incorporated into their genome a human or rodent fra-2 DNA. The fra-2 transgenic cells can be obtained from a rodent with ectopic expression of fra-2 either in a ubiquitous manner or specifically in the cell type of interest. The cells are selected with regard to their ability to contribute to development of the fibrotic disease, in particular pulmonary fibrosis, e.g. hematopoietic cells, pulmonary epithelial or mesenchymal cells like fibroblasts or myofibroblasts. Since excessive growth of fibroblasts on the one hand and formation of myofibroblasts (resulting from transformation of fibroblast or originating from hematopoietic cells) on the other hand are relevant for the phenotype of pulmonary disease, fibroblasts and myofibroblasts are of particular interest.

Cells of interest can be isolated and cultivated according to known methods, e.g. fibroblasts, myofibroblasts, lung epithelial cells (Dong et al., 1997; Phipps et al., 1989).

Alternatively to isolating the cells of interest from the transgenic animals, the respective primary cells or cell lines can be transfected with fra-2 DNA.

The fra-$2^{tg}$ mice and cells derived therefrom are useful for testing drugs for the treatment of fibrotic diseases like pulmonary disease.

The animal model of the invention can also be used to test therapeutic strategies, e.g. compounds, for avoiding abnormal scar formation by pharmacological intervention. In particular fra-$2^{tg}$ mice or fra-$2^{tg}$ cells can be used in assays to screen for inhibitors of scar formation in excessive healing. The experiments of the invention have proven that Fra-2 itself is a target for pharmacological intervention of fibrotic disorders, including excessive scar formation. Therefore, Fra-2 inhibitors may be useful as inhibitors for such diseases.

The animal model of the invention may be used, but is not limited to evaluate inhibitors of pro-inflammatory cytokines that play a role in fibrogenic pathways that depend on Fra-2 activity. For instance, novel inhibitors that might prevent microinjury of pulmonary epithelial cells, such as angiotensin converting enzyme inhibitors or caspase inhibitors can be tested in the animal model of the invention. Also, specific inhibitors that prevent the accumulation of collagen or in general the fibrogenic activity of cells in fibrotic foci of affected lungs can be tested.

According to a further aspect of the invention, the transgenic animal and cell lines derived therefrom can also be used to identify or test candidate compounds effective in the therapy of fibrotic disease, in particular pulmonary fibrosis, e.g. by inhibiting not yet identified fibrogenic pathways that are dependent on Fra-2 activity.

Thus, the present invention further provides a method of determining a compound's therapeutic effect on a fibrotic disease, e.g. pulmonary fibrosis. The method includes administering an effective amount of a test compound to a fra-$2^{tg}$ rodent, in particular a mouse. The method includes measuring the response of the transgenic animal to the test compound (i.e. the amelioration or disappearance of the disease symptoms), and comparing the response of the transgenic animal to a control animal, which may be, for example, a wild-type animal or alternatively, a transgenic animal control. Compounds that may have an effect on the phenotype resulting from ectopic fra-2 expression may also be screened against cells in cell-based assays, for example, to identify such compounds. In assays using cells that overexpress fra-2, the compounds can be tested for their effect on excessive growth of fibroblasts and/or on transformation of fibroblasts to myofibroblasts and/or extracellular matrix formation.

Toxicity and therapeutic efficacy of the identified compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. For example, achieving topical selectivity by way of inhaled compounds with short plasma half-lives to treat lung fibrosis.

The data obtained from the cell culture assays and animal studies can be used in formulating a range of dosage for use in humans. The dosage of such compounds lies preferably within a range of circulating concentrations that include the $ED_{50}$ with little or no toxicity. If the therapeutic window allows the use higher ED values without toxic effects, such ED values, e.g. up to $ED_{90}$, are preferred.

The dosage may vary within this range depending upon the dosage form employed and the route of administration utilized. For any compound, the therapeutically effective dose can be estimated initially from cell culture assays. A dose may be formulated in an animal models to achieve a circulating plasma concentration range that includes the $IC_{50}$ (i.e., the concentration of the test compound that achieves a half-maximal inhibition of symptoms) or higher as determined in cell culture. (For agonists, values above the IC50 value (or the ED50 value for agonists) are preferred).

Such information can be used to more accurately determine useful doses in humans. Levels in plasma may be measured according to known methods, for example, by high performance liquid chromatography.

Finally, the animal model is useful to study the etiology of human fibrotic diseases, e.g. pulmonary fibrosis. It is very important defining the cell type that is responsible for development of pulmonary fibrosis. The conventional bleomycin-induced pulmonary fibrosis models do not allow experiments such as bone marrow transplantation studies which hamper this goal. In addition, fra-2$^{tg}$ mice can be bred into different genetic backgrounds such as mice with Rag2 deficiency or loss of TNF-α receptor p55 function to evaluate the contribution of autoreactive T-cells and TNF-signaling to pulmonary fibrosis, respectively. The knowledge about the responsible cell type and the major signaling pathways that can be obtained with the animal model according to the invention has a pivotal influence on the general direction of drug testing for treatment of pulmonary fibrosis.

In the Examples, the following materials and methods were used:

Generation of fra-2$^{tg}$ Mice

The fra-2 full-length locus is isolated from a genomic λ DNA library, sequenced and cloned into the pBS II vector. The promoter for the major histocompatibility complex class I antigen H2-K$^b$ (Grigoriadis et al., 1993) is cloned in front of the fra-2 genomic locus to allow ubiquitous transgene expression. To monitor transgene activity, an IRES-EGFP (Zhu et al., 1999) sequence is cloned behind the fra-2 locus followed by the long terminal repeat (LTR) sequence of the FBJ-murine sarcoma virus (Grigoriadis et al., 1993). In addition, a loxP sites is placed in front of exon 2 and after exon 4 to allow Cre-mediated deletion of transgene multimers and generation of several transgenic lines with different transgene copy numbers. The transgenic construct is injected into the pronucleus of fertilized C57B176 oocytes and three independent transgenic lines are established.

Southern Blot and RNase Protection Assay (RPA)

For the fra-2 Southern blot, 10 μg of tail DNA is digested with HindIII yielding a 12.5 kb fragment for the wild-type fra-2 allele and a 7.5 kb fragment for the transgene. For detection of the bands a 0.6 kb KpnI fragment corresponding to exon 2 of fra-2 is used as probe. For the RNase protection assay total lung RNA is isolated with the TRIZOL protocol (Sigma). RNase protection assays are performed using the RiboQuant multi-probe RNase protection assay systems mCK-2b and mCK-5c (PharMingen) according to the manufacturer's protocol.

Histology

Tissues are fixed overnight with neutral buffered 4% PFA at 4° C. and embedded in paraffin. Five-micrometer sections are stained either with hematoxylin and eosin (H&E) or chromanilineblue or processed further. Immunohistochemical staining for anti CD3 (Santa Cruz) is performed after antigen-retrieval (Dako S1699) with the MultiLink Dako system (Dako E0453) according to the manufacturer's recommendations.

Bone Marrow Reconstitution 6-10 month old female recipient mice are lethally irradiated and reconstituted 20 hours later with bone marrow from male donor mice. Bone marrow is flushed out of femurs and tibias of donor mice, counted, and 5×10$^6$ cells are injected into the tail vein of recipients. Bone marrow and spleen cells from recipients were taken routinely after they were sacrificed for histological examination and the efficiency of reconstitution is evaluated by Southern Blot and FACS analysis for EGFP-fluorescence.

EXAMPLE 1

Generation and Characterization of fra-2$^{tg}$ Mice

The genomic fra-2 locus is placed on a transgenic vector with the broadly active H2K$^b$ promoter in front and an IRES-EGFP reporter gene behind (FIG. 1A). A long terminal repeat (LTR) sequence of the FBJ-murine sarcoma virus is included for stabilization of fra-2 mRNA and to ensure transgene expression in mesenchymal cells. The additional loxP sites that are placed in front of exon 2 and after exon 4 allow Cre-mediated deletion of transgene multimers and generation of several transgenic lines with different transgene copy numbers and levels of transgene expression. Three independent transgenic lines with different transgene copy numbers are generated (FIG. 1B). Line 12 and 13 express the transgene at high levels (FIG. 1C) and carry 4 and 60 transgene copies, respectively. Line 15 carries only two transgene copies and did not show any overt transgene expression (FIG. 1C). Considerable transgene expression can be observed in all tissues of lines 12 and 13 except for the brain (FIG. 1D).

EXAMPLE 2

Pulmonary Fibrosis Develops in fra-2$^{tg}$ Mice

Figure 2:
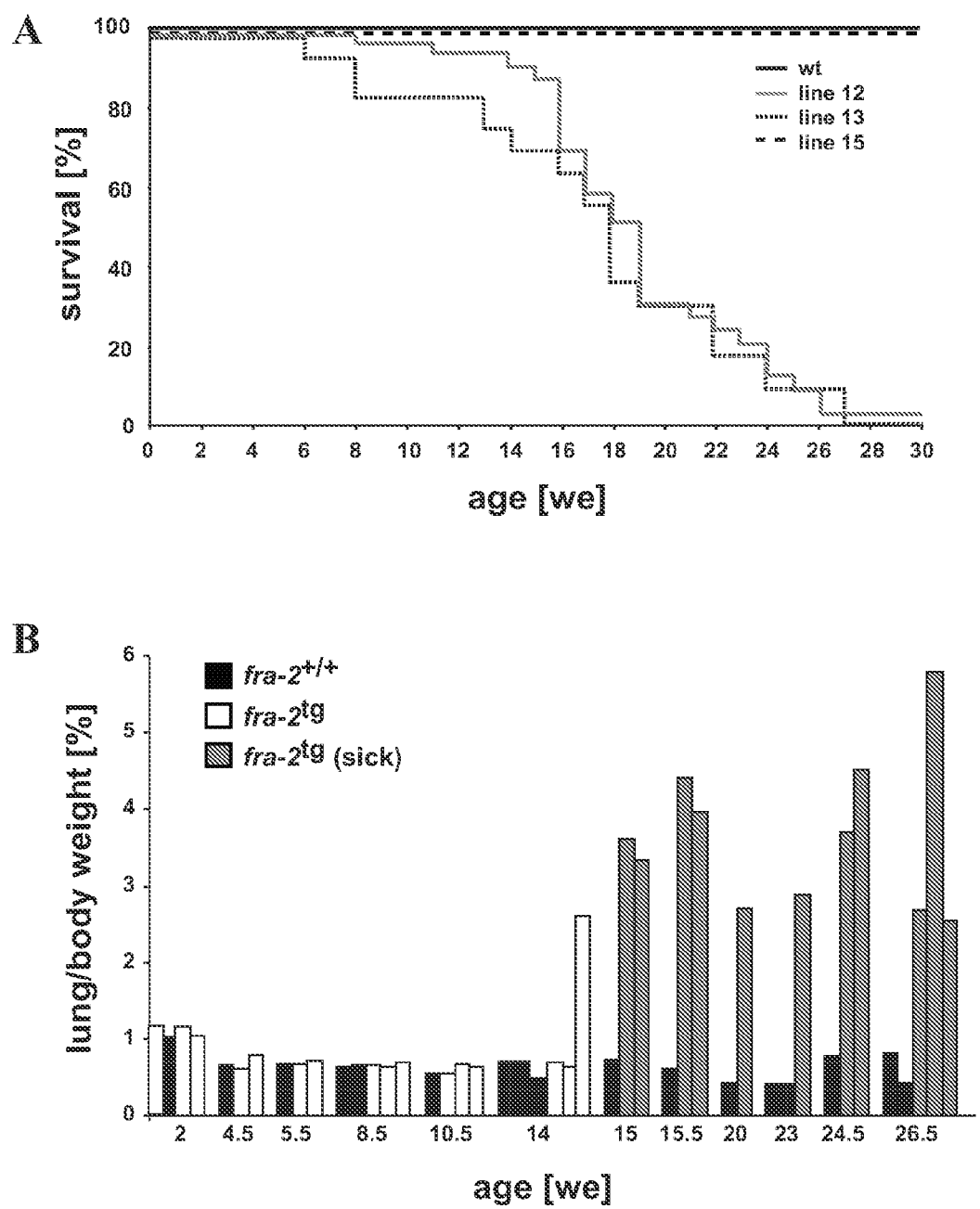
Figure 3:
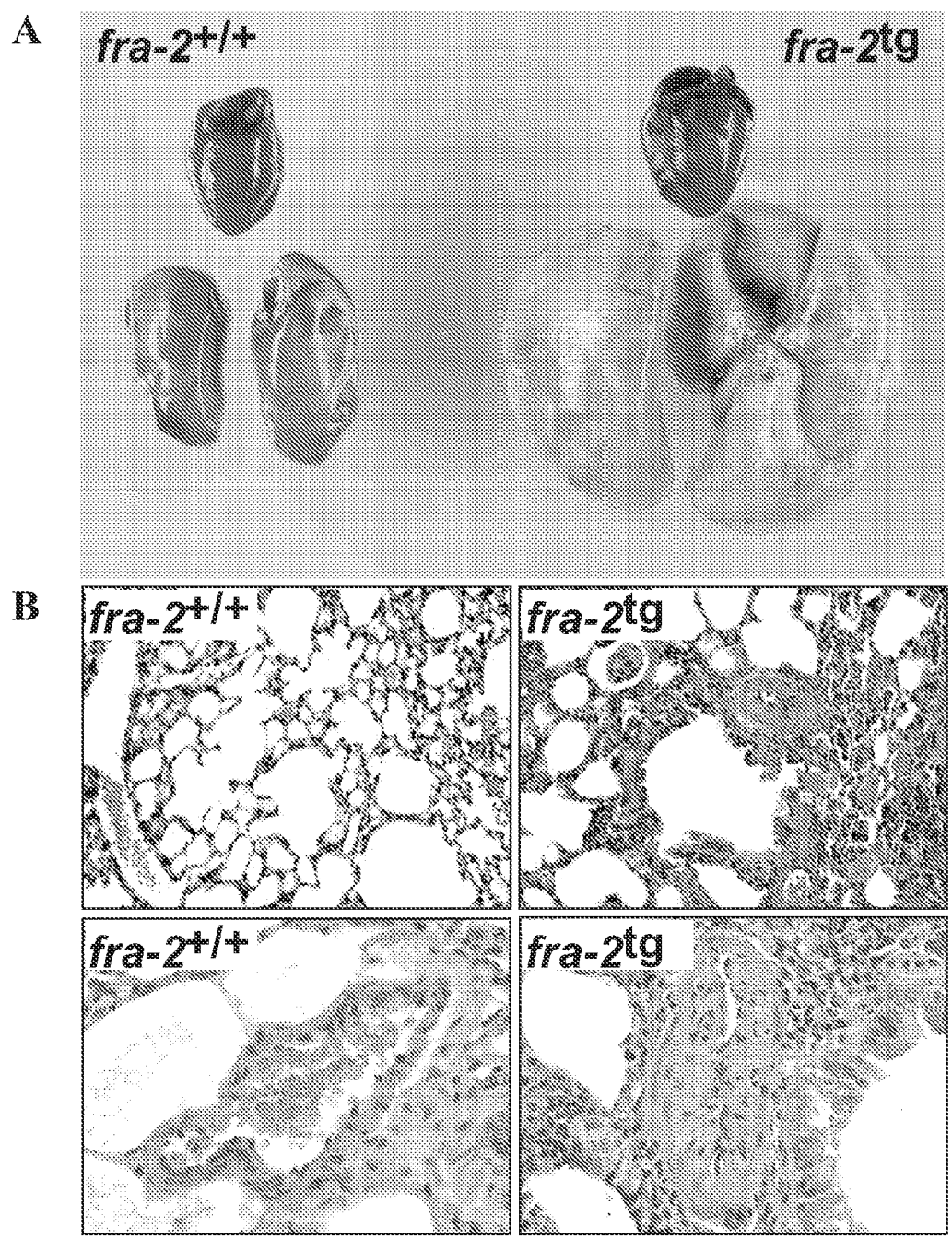
Figure 4A:
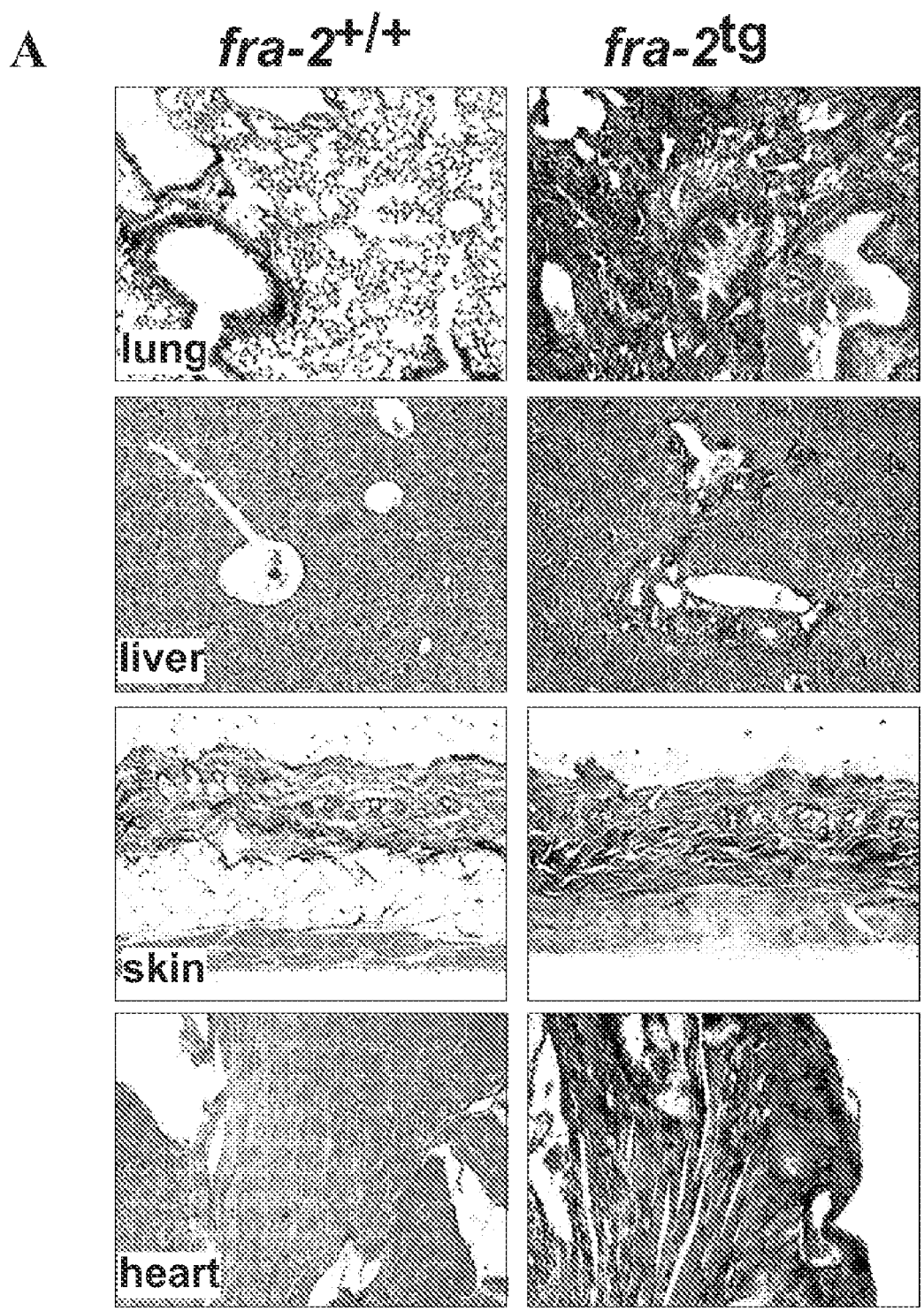
Figure 4B:
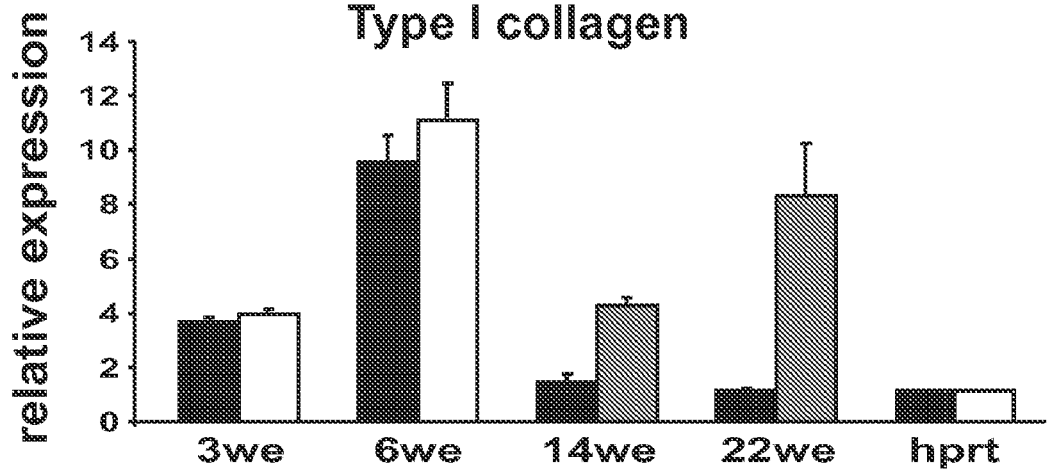
Figure 4B:
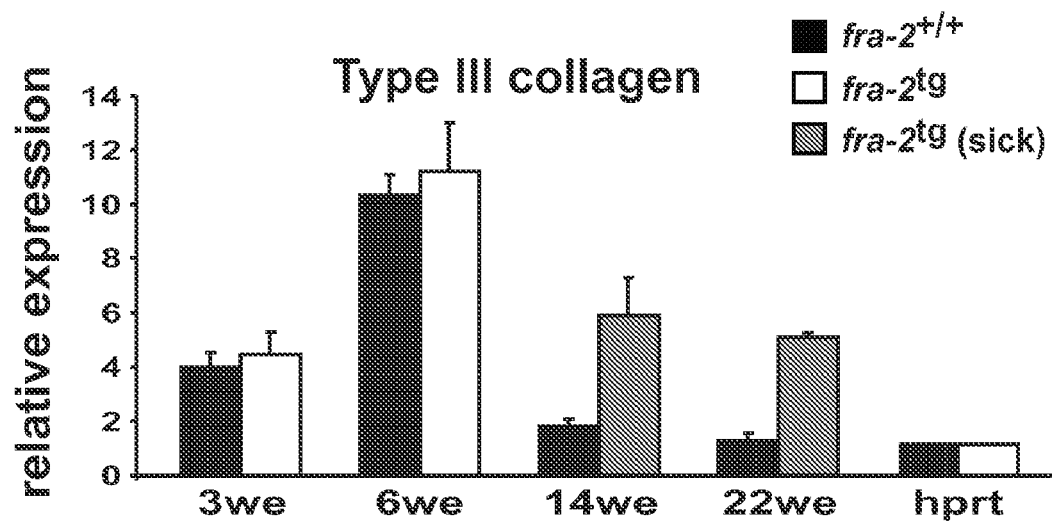

The major phenotype that the mice develop is generalized fibrosis with an emphasis on lung tissue. Pulmonary fibrosis is responsible for the premature lethality of the majority of fra-2$^{tg}$ mice (FIG. 2A). Mice become sick around 12 months of age and suffer from shortness of breath which is due to a dramatic increase in lung weight (FIGS. 2B, 3A) and fibrosis of lung tissue (FIG. 3B). Pulmonary fibrosis often develops in response to environmental pollutants or in the context of a syndrome. Collagen-staining of several tissues has demonstrated that the pulmonary fibrosis in fra-2$^{tg}$ mice develops in the context of a scleroderma-like disease which is characterized by a generalized fibrosis in several tissues (FIG. 4A). Increased production of fibrogenic collagens in the lung is confirmed by real-time PCR analysis.

EXAMPLE 3

Inflammation is One of the First Events in Pulmonary Fibrosis

Figure 5A:
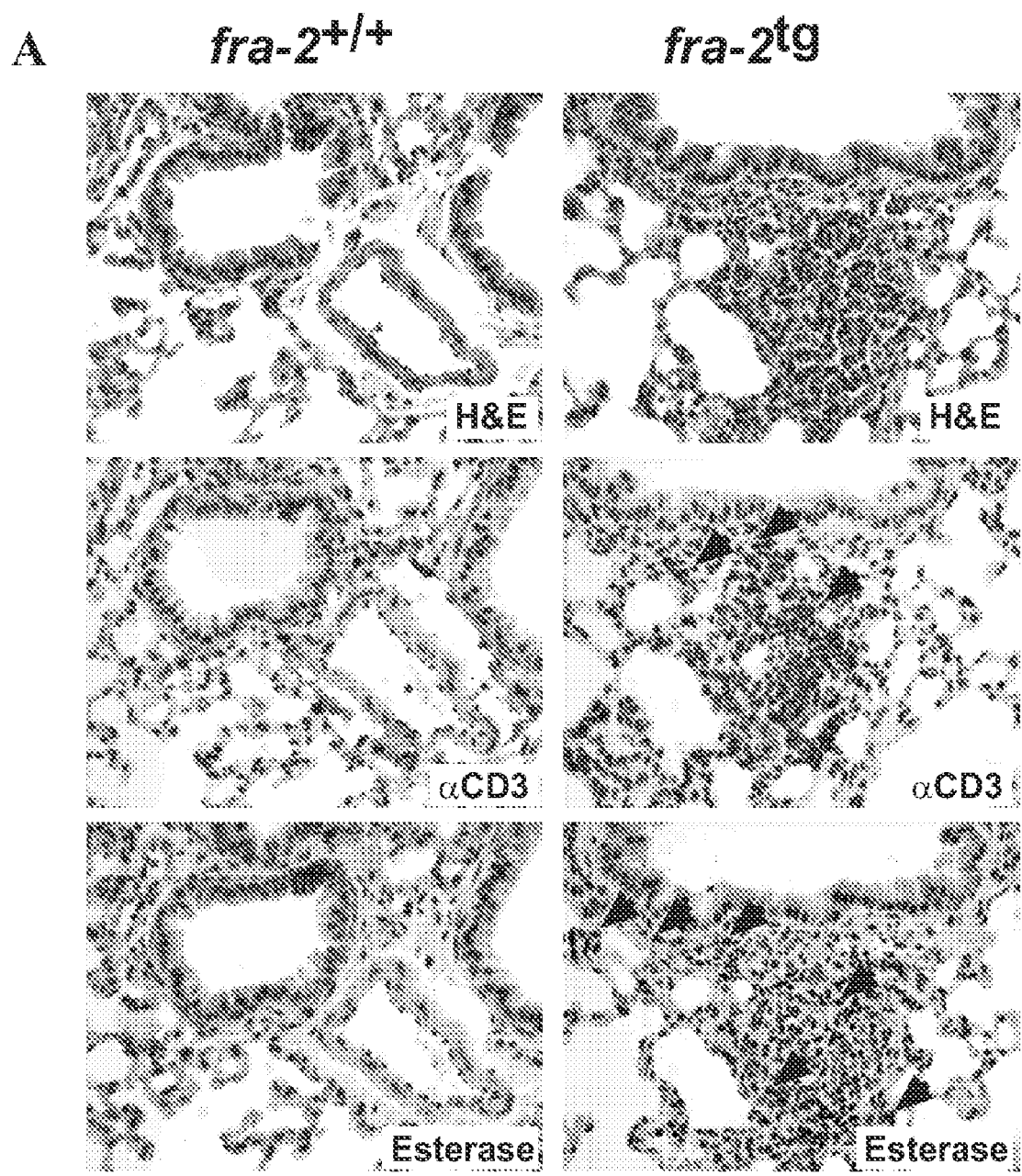
Figure 5B:
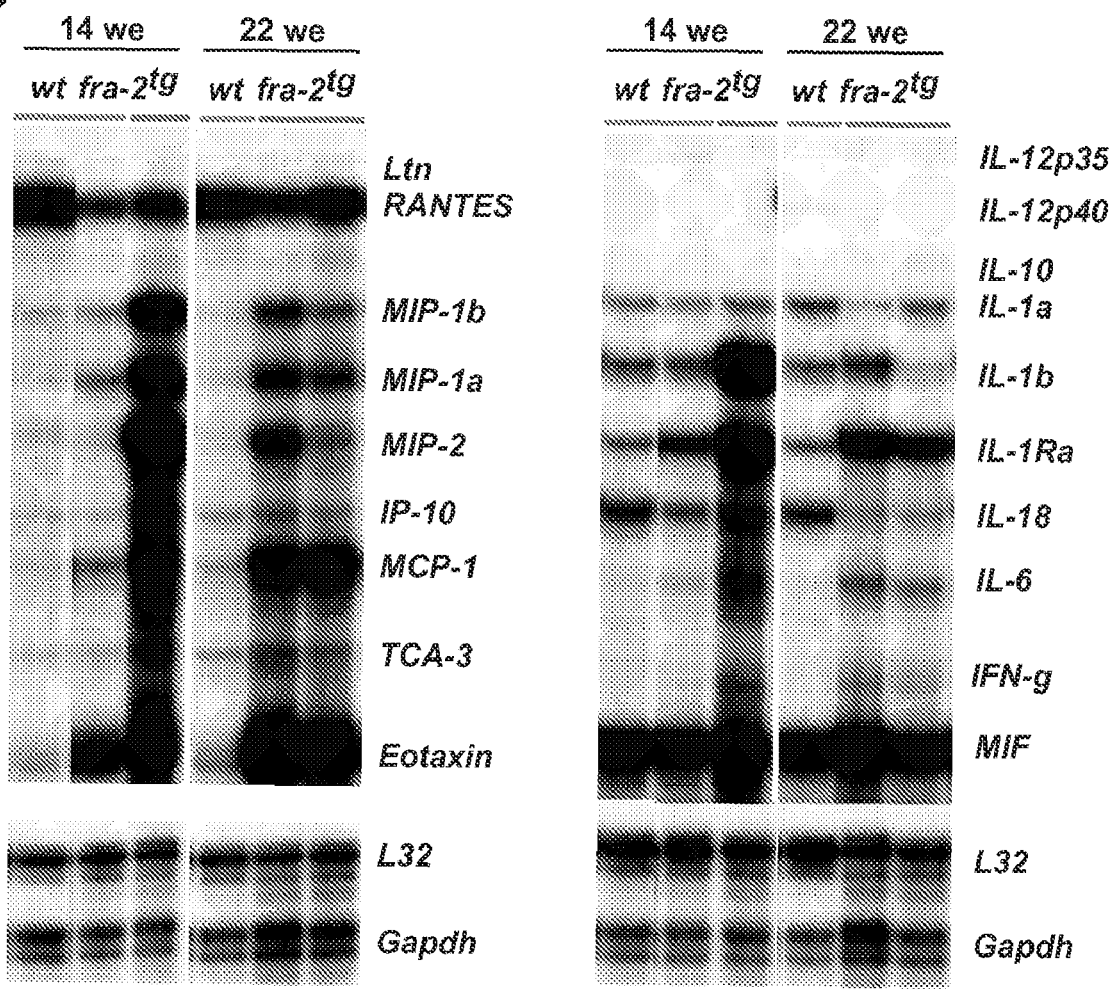
Figure 6A:
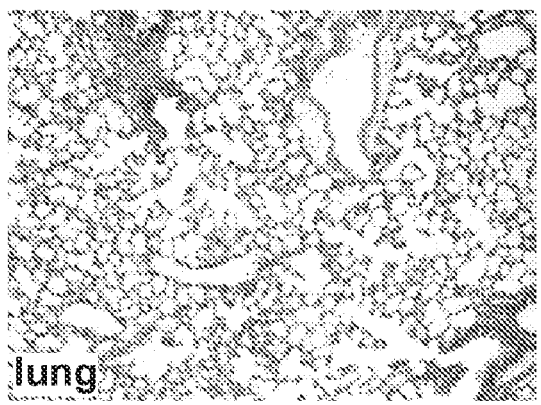
Figure 6A:
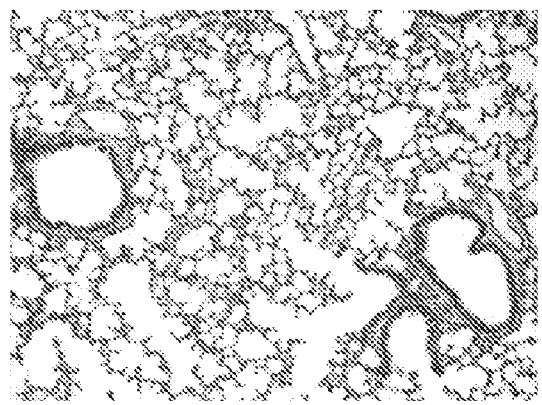
Figure 6A:
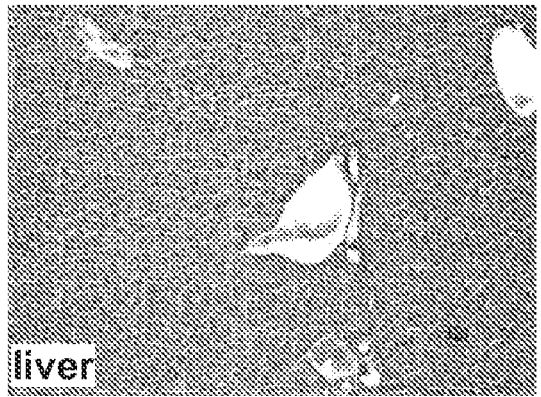
Figure 6A:
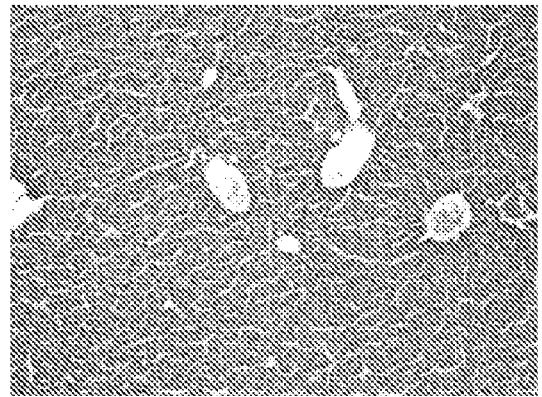

Lungs of 10-14 week-old mice are analysed in order to identify the starting events of pulmonary fibrosis in fra-2$^{tg}$ mice. This analysis has demonstrated that inflammation in the vascular and perivascular regions is one of the first events in pulmonary fibrosis (FIG. 5A). Immunohistochemical and histochemical stainings identify the major cell populations that infiltrate the lung. These are CD3-positive T-cells and esterase-positive myeloid cells (FIG. 5A). The presence of these cells is associated with increased levels of chemokines and cytokines (FIG. 5B) which might contribute to the fibrogenic changes in the lung and might also attract more inflammatory cells.

EXAMPLE 4

Figure 7A:
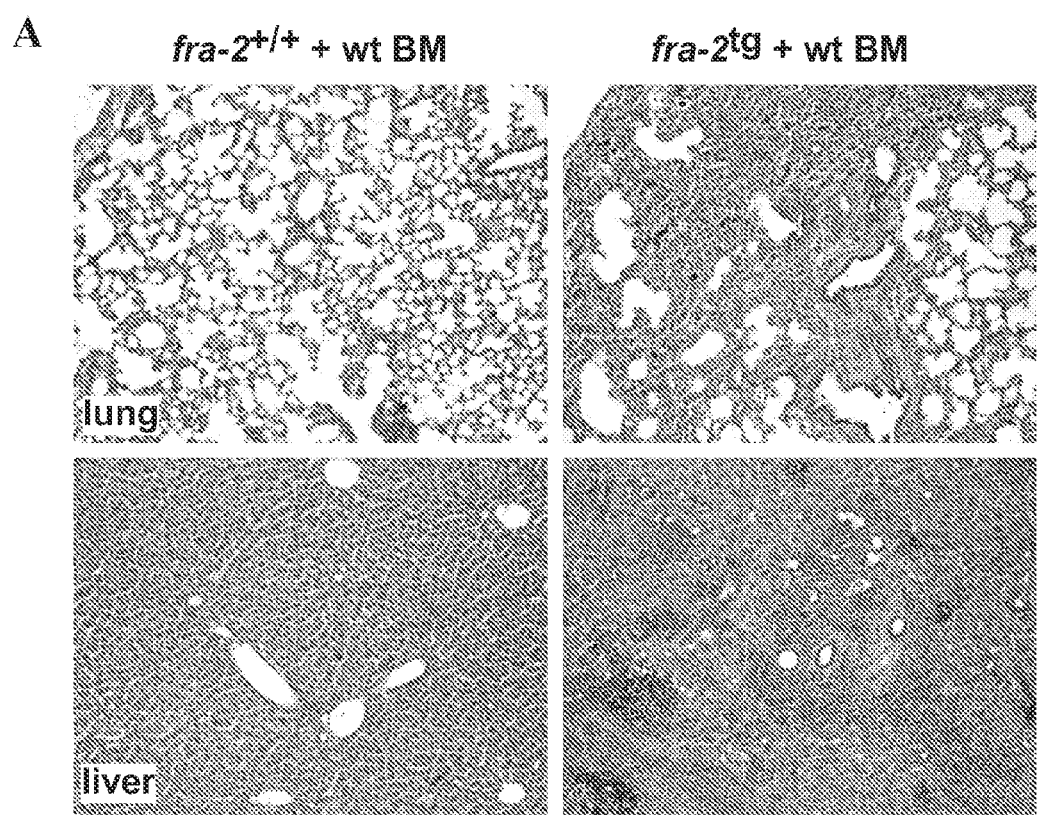

Inflammation and Pulmonary Fibrosis are Triggered by Microinjury of Airway Epithelial Cells It is still a matter of debate if pulmonary fibrosis is primarily an autoimmune disease or if it is triggered by microinjury of airway epithelia with a more or less important contribution of the immune system. These questions are addressed by bone marrow transplantation experiments. On the one hand, the disease should be transplantable with fra-2$^{tg}$ bone marrow in case that fra-2$^{tg}$ mice develop autoreactive immune cells that are responsible for lung damage and pulmonary fibrosis. On the other hand, the disease should also develop in fra-2$^{tg}$ mice that have been reconstituted with wild-type bone marrow cells in case that microinjury of airway epithelia is the primary trigger of the fibrosis. Preliminary data suggest that the pulmonary fibrosis cannot be easily transplanted with fra-2$^{tg}$ bone marrow cells excluding an autoimmune disease as the primary cause (FIG. 6). However, a severe pulmonary fibrosis seems to develop in fra-2$^{tg}$ mice reconstituted with wild-type bone marrow (FIG. 7). These data suggest that a microinjury process, most likely caused by apoptosis of alveolar epithelial cells, is the primary cause of pulmonary fibrosis.

EXAMPLE 5

Fra-2$^{tg}$ Mice Show Excessive Scar Formation

Figure 8C:
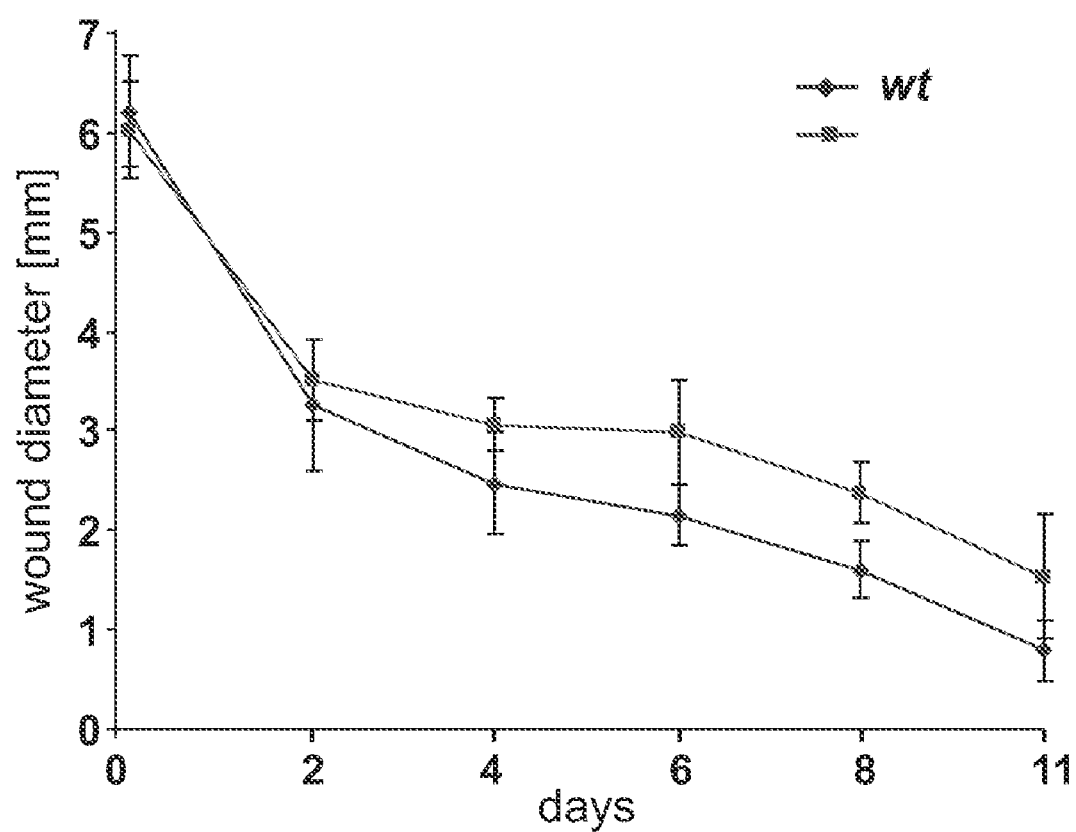

Fra-2$^{tg}$ mice show delayed wound closure after full-thickness skin biopsy punch wounding of the backskin (FIGS. 8A,C). An increased amount of granulation tissue consisting of collagen is visible in the wounds of fra-2$^{tg}$ mice after wounding (FIG. 8B). Rnase protection assays with skin biopsies taken at wounding and 3 days after wounding demonstrate no differences in expression of AP-1 members (except for fra-2), matrix metalloproteinases, TIMPs, cytokines, TGF-beta family members and chemokines (FIG. 8D-G). These data demonstrate that increased Fra-2 activity leads to a delay in wound closure and to excessive scar formation. This suggests that inhibitors of Fra-2 activity can be applied ectopically to avoid scar formation after injury or surgery.

REFERENCES

Behrens, A., Haigh, J., Mechta-Grigoriou, F., Nagy, A., Yaniv, M., and Wagner, E. F. (2003). Impaired intervertebral disc formation in the absence of Jun. Development 130, 103-109.
Blesch, A. (2004). Lentiviral and MLV based retroviral vectors for ex vivo and in vivo gene transfer. Methods 33, 164-172.
Boggaram, V. (2003). Regulation of lung surfactant protein gene expression. Front Biosci 8, d751-764.
Clausen, B. E., Burkhardt, C., Reith, W., Renkawitz, R., and Forster, I. (1999). Conditional gene targeting in macrophages and granulocytes using LysMcre mice. Transgenic Res 8, 265-277.
Dong, Q. G., Bernasconi, S., Lostaglio, S., De Calmanovici, R. W., Martin-Padura, I., Breviario, F., Garlanda, C., Ramponi, S., Mantovani, A., and Vecchi, A. (1997). A general strategy for isolation of endothelial cells from murine tissues. Characterization of two endothelial cell lines from the murine lung and subcutaneous sponge implants. Arterioscler Thromb Vasc Biol 17, 1599-1604.
Chang W, Rewari A, Centrella M, McCarthy T L. Fos-related antigen 2 controls protein kinase A-induced CCAAT/enhancer-binding protein beta expression in osteoblasts. J Biol Chem. 2004 October 8; 279(41):42438-44.
Du, W., Thanos, D., and Maniatis, T. (1993). Mechanisms of transcriptional synergism between distinct virus-inducible enhancer elements. Cell 74, 887-898.
Eferl, R., Hoebertz, A., Schilling, A. F., Rath, M., Karreth, F., Kenner, L., Amling, M., and Wagner, E. F. (2004). The Fos-related antigen Fra-1 is an activator of bone matrix formation. Embo J 23, 2789-2799. Epub 2004 July 2701.
Eferl, R., and Wagner, E. F. (2003). AP-1: a double-edged sword in tumorigenesis. Nat Rev Cancer 3, 859-868.
Fleischmann, A., Hafezi, F., Elliott, C., Reme, C. E., Ruther, U., and Wagner, E. F. (2000). Fra-1 replaces c-Fos-dependent functions in mice. Genes Dev 14, 2695-2700.
Foletta, V. C., Sonobe, M. H., Suzuki, T., Endo, T., Iba, H., and Cohen, D. R. (1994). Cloning and characterisation of the mouse fra-2 gene. Oncogene 9, 3305-3311.
Gir, S. N. (2003). Novel pharmacological approaches to manage interstitial lung fibrosis in the twenty-first century. Annu Rev Pharmacol Toxicol 43, 73-95. Epub 2002 January 2010.
Grigoriadis, A. E., Schellander, K., Wang, Z. Q., and Wagner, E. F. (1993). Osteoblasts are target cells for transformation in c-fos transgenic mice. J Cell Biol 122, 685-701.
Grigoriadis, A. E., Wang, Z. Q., Cecchini, M. G., Hofstetter, W., Felix, R., Fleisch, H. A., and Wagner, E. F. (1994). c-Fos: a key regulator of osteoclast-macrophage lineage determination and bone remodeling. Science 266, 443-448.
Gross, T. J., and Hunninghake, G. W. (2001). Idiopathic pulmonary fibrosis. N Engl J Med 345, 517-525.
Hashimoto, N., Jin, H., Liu, T., Chensue, S. W., and Phan, S. H. (2004). Bone marrow-derived progenitor cells in pulmonary fibrosis. J Clin Invest 113, 243-252.
Jochum, W., David, J. P., Elliott, C., Wutz, A., Plenk, H., Jr., Matsuo, K., and Wagner, E. F. (2000). Increased bone formation and osteosclerosis in mice overexpressing the transcription factor Fra-1. Nat Med 6, 980-984.
Jochum, W., Passegue, E., and Wagner, E. F. (2001). AP-1 in mouse development and tumorigenesis. Oncogene 20, 2401-2412.
Karreth, F., Hoebertz, A., Scheuch, H., Eferl, R., and Wagner, E. F. (2004). The AP1 transcription factor Fra2 is required for efficient cartilage development. Development 131, 5717-5725.
Kenner, L., Hoebertz, A., Beil, T., Keon, N., Karreth, F., Eferl, R., Scheuch, H., Szremska, A., Amling, M., Schorpp-Kistner, M., et al. (2004). Mice lacking JunB are osteopenic due to cell-autonomous osteoblast and osteoclast defects. J Cell Biol 164, 613-623. Epub 2004February 2009.
Krein, P. M., and Winston, B. W. (2002). Roles for insulin-like growth factor I and transforming growth factor-beta in fibrotic lung disease. Chest 122, 289S-293S.
Lai, C. M., Lai, Y. K., and Rakoczy, P. E. (2002). Adenovirus and adeno-associated virus vectors. DNA Cell Biol 21, 895-913.
Matsui, M., Tokuhara, M., Konuma, Y., Nomura, N. and Ishizaki, R. Isolation of human fos-related genes and their expression during monocyte-macrophage differentiation. Oncogene 5 (3), 249-255 (1990)

Miyazaki, Y., Araki, K., Vesin, C., Garcia, I., Kapanci, Y., Whitsett, J. A., Piguet, P. F., and Vassalli, P. (1995). Expression of a tumor necrosis factor-alpha transgene in murine lung causes lymphocytic and fibrosing alveolitis. A mouse model of progressive pulmonary fibrosis. J Clin Invest 96, 250-259.

Ortiz, L. A., Lasky, J., Hamilton, R. F., Jr., Holian, A., Hoyle, G. W., Banks, W., Peschon, J. J., Brody, A. R., Lungarella, G., and Friedman, M. (1998). Expression of TNF and the necessity of TNF receptors in bleomycin-induced lung injury in mice. Exp Lung Res 24, 721-743.

Phipps, R. P., Penney, D. P., Keng, P., Quill, H., Paxhia, A., Derdak, S., and Felch, M. E. (1989). Characterization of two major populations of lung fibroblasts: distinguishing morphology and discordant display of Thy 1 and class II MHC. Am J Respir Cell Mol Biol 1, 65-74.

Piguet, P. F., Collart, M. A., Grau, G. E., Kapanci, Y., and Vassalli, P. (1989). Tumor necrosis factor/cachectin plays a key role in bleomycin-induced pneumopathy and fibrosis. J Exp Med 170, 655-663.

Piguet, P. F., Kaufman, S., Barazzone, C., Muller, M., Ryffel, B., and Eugster, H. P. (1997). Resistance of TNF/LT alpha double deficient mice to bleomycin-induced fibrosis. Int J Exp Pathol 78, 43-48.

Rickert, R. C., Roes, J., and Rajewsky, K. (1997). B lymphocyte-specific, Cre-mediated mutagenesis in mice. Nucleic Acids Res 25, 1317-1318.

Rossert J., Eberspaecher H. and de Crombrugghe B. (1995) Separate cis-acting DNA elements of the mouse pro-alpha 1(I) collagen promoter direct expression of reporter genes to different type I collagen-producing cells in transgenic mice. J of Cell Biology, Vol 129, 1421-1432, Sabatakos, G., Sims, N. A., Chen, J., Aoki, K., Kelz, M. B., Amling, M., Bouali, Y., Mukhopadhyay, K., Ford, K., Nestler, E. J., and Baron, R. (2000). Overexpression of DeltaFosB transcription factor(s) increases bone formation and inhibits adipogenesis. Nat Med 6, 985-990.

Schorpp, M., Jager, R., Schellander, K., Schenkel, J., Wagner, E. F., Weiher, H., and Angel, P. (1996). The human ubiquitin C promoter directs high ubiquitous expression of transgenes in mice. Nucleic Acids Res 24, 1787-1788.

Selman, M., and Pardo, A. (2003). The epithelial/fibroblastic pathway in the pathogenesis of idiopathic pulmonary fibrosis. Am J Respir Cell Mol Biol 29, S93-97.

Stein, B., Baldwin, A. S., Jr., Ballard, D. W., Greene, W. C., Angel, P., and Herrlich, P. (1993). Cross-coupling of the NF-kappa B p65 and Fos/Jun transcription factors produces potentiated biological function. Embo J 12, 3879-3891.

Tanigaki, K., Tsuji, M., Yamamoto, N., Han, H., Tsukada, J., Inoue, H., Kubo, M., and Honjo, T. (2004). Regulation of alphabeta/gammadelta T cell lineage commitment and peripheral T cell responses by Notch/RBP-J signaling. Immunity 20, 611-622.

Wang, Z. Q., Ovitt, C., Grigoriadis, A. E., Mohle-Steinlein, U., Ruther, U., and Wagner, E. F. (1992). Bone and haematopoietic defects in mice lacking c-fos. Nature 360, 741-745.

Wolf, S. E., and Woodside, K. J. (2005). Transgenic and gene knock-out techniques and burn research. J Surg Res 123, 328-339.

Zhu, J., Musco, M. L., and Grace, M. J. (1999). Three-color flow cytometry analysis of tricistronic expression of eBFP, eGFP, and eYFP using EMCV-IRES linkages. Cytometry 37, 51-59.

The invention claimed is:

1. A non-human animal model for fibrotic diseases, comprising a fra-2 transgenic mouse with a fra-2 transgene encoding a murine, rat or human genomic fra-2 locus operably linked to a $H2k^b$ promoter, wherein said fra-2 transgene is broadly and ectopically over-expressed resulting in a broad ectopic expression of fra-2 that manifests itself in a phenotype comprising excessive growth of fibroblasts and/or transformation of fibroblasts to myofibroblasts and/or extracellular matrix formation or scleroderma-like generalized fibrosis, and excluding a perturbation of normal eye development.

2. The model of claim 1, wherein said fra-2 transgene is ectopically expressed in lung cells and the phenotype comprises pulmonary fibrosis.

3. The model of claim 1, wherein the phenotype comprises excessive scar formation in the skin.

4. The model according to claim 1, wherein said over-expression of fra-2 occurs in mesenchymal cells.

5. The model according to claim 4, wherein said mesenchymal cells are fibroblasts or myofibroblasts.

6. The model according to claim 1, wherein said fra-2 locus is murine.

7. A method of determining a test compound's effect on a phenotype resulting from ectopic fra-2 over-expression, comprising:
(a) contacting control cells with a test compound,
(b) observing the effect of said test compound on the control cells,
(c) contacting test cells isolated from the fra-2 transgenic mouse of claim 1 with a test compound, wherein the test cells are selected from the group consisting of fibroblasts, myofibroblasts, hematopoietic cells and pulmonary epithelial cells,
(d) observing the effect of said test compound on said test cells on the phenotype resulting from ectopic fra-2 over-expression, and
(e) comparing the effect of said test compound on said test cells to the effect of said test compound on said control cells.

8. The method of claim 7, wherein said test cells are hematopoietic cells.

9. The method of claim 7, wherein said test cells are pulmonary epithelial cells.

* * * * *